United States Patent [19]

Sekmakas et al.

[11] Patent Number: 4,535,122
[45] Date of Patent: Aug. 13, 1985

[54] WET ADHESION PROMOTERS FOR EMULSION POLYMERS

[75] Inventors: Kazys Sekmakas, Palatine; Raj Shah, Schaumburg, both of Ill.

[73] Assignee: DeSoto, Inc., Des Plains, Ill.

[21] Appl. No.: 655,544

[22] Filed: Sep. 28, 1984

Related U.S. Application Data

[62] Division of Ser. No. 511,993, Jul. 8, 1983, Pat. No. 4,487,941.

[51] Int. Cl.$^3$ ............... C08F 26/06; C08L 39/04
[52] U.S. Cl. ........................ 524/809; 526/260
[58] Field of Search .................. 524/809; 526/260

[56] References Cited

U.S. PATENT DOCUMENTS

| | | | |
|---|---|---|---|
| 3,356,653 | 12/1967 | Sekmakas | 524/809 |
| 3,356,654 | 12/1967 | Sekmakas | 524/809 |
| 3,514,473 | 5/1970 | McFadden | 526/260 |
| 3,829,407 | 8/1974 | McKillip | 526/260 |
| 4,104,220 | 8/1978 | Sims | 524/809 |
| 4,111,877 | 9/1978 | Dixon | 524/809 |
| 4,429,095 | 1/1984 | Sandri | 524/809 |
| 4,436,887 | 3/1984 | Chromecek | 526/260 |
| 4,440,919 | 4/1984 | Chromecek | 526/260 |
| 4,490,491 | 12/1984 | Devona | 524/809 |

*Primary Examiner*—C. Warren Ivy
*Attorney, Agent, or Firm*—Dressler, Goldsmith, Shore, Sutker & Milnamow, Ltd.

[57] ABSTRACT

An acrylate or methacrylate functional copolymerizable monomer which serves as an adhesion for emulsion polymers is disclosed. This monomer is the adduct formed by reacting an aminoalkyl alkylene urea with about 0.9 up to about 1.5 molar proportions of a saturated monoepoxide to consume most or all of one of the two amino hydrogen atoms available, and then reacting with about 0.8 up to about 2.0 molar proportions of glycidyl acrylate, glycidyl methacrylate, or a mixture thereof in the presence of at least 0.02%, based on the total weight of the reactants present, of an inhibitor which retards the free-radical polymerization of ethylenic unsaturation, such as hydroquinone, and phenothiazine.

3 Claims, No Drawings

4,535,122

WET ADHESION PROMOTERS FOR EMULSION POLYMERS

This application is a division of application Ser. No. 511,993 filed July 8, 1983 and now U.S. Pat. No. 4,487,941.

DESCRIPTION

1. Technical Field

This invention relates to acrylate or methacrylate functional copolymerizable monomers which enhance the adhesion of emulsion copolymer latices to an underlying substrate, to the production of such monomers, to copolymers containing the same, and to latex emulsions.

2. Background Art

The emulsion copolymerization of monoethylenically unsaturated monomers to produce latex emulsions for paints is well known. It is also known to include a small proportion of a monoethylenically unsaturated amine-functional monomer in the monomers which are copolymerized in order to improve the adhesion (both wet and dry) of the latex paint to the substrate which is painted. The objective is to provide the greatest improvement in adhesion in the simplest and most effective manner, the cost being a material factor in achieving this objective.

The prior efforts in this direction are illustrated by U.S. Pat. No. 3,356,653 to K. Sekmakas, but there are many other patents which are concerned, in one way or another, with the same problem.

Another patent of interest to this problem and to this invention is U.S. Pat. No. 3,509,085 to K. Sekmakas which describes the production of unsaturated hydroxy functional cyclic amine ethers which are useful for promoting the adhesion of emulsion polymers. These monomers are prepared by reacting an unsaturated monoepoxide, such as glycidyl acrylate or allyl glycidyl ether, with 2-hydroxyethyl ethylene urea.

A recent patent of interest is U.S. Pat. No. 4,319,032 to J. M. Sandri et al. in which the adhesion-promoting monomer is produced by the reaction of an omega aminoalkyl alkylene urea, such as 2-amino-ethyl ethylene urea, with an unsaturated glycidyl ether or ester. Allyl glycidyl ether is primarily contemplated, but glycidyl methacrylate is also suggested for use. Since many of the monomers which one would wish to have present in an emulsion copolymer polymerize better with acrylate or methacrylate unsaturation than with allylic unsaturation, it would be better to be able to use glycidyl methacrylate. However, when this was attempted in the Sandri et al. disclosure, they reported an increase in viscosity, which is detrimental. Of greater concern is the fact that the increased viscosity is accompanied by instability, the monomer product sometimes gelling while it is being made, and more frequently gelling within a few hours or a few days after production. The problem seems to be the fact that the acrylate or methacrylate unsaturation tends to polymerize and also to Michael adduct with the amino hydrogen atoms, these two actions tending to increase viscosity. The subsequent gelation at room temperature or below is more mysteriouss because the amino hydrogen atoms may no longer be present and polymerization generally requires higher temperature. In any event, these actions effectively prevent the use of even glycidyl methacrylate in the Sandri et al. environment as a practical matter (though not as a matter of scientific curiosity).

DISCLOSURE OF INVENTION

In accordance with this invention, an aminoalkyl alkylene urea is first reacted with a saturated monoepoxide to consume most or all of one of the two amino hydrogen atoms which are available and to leave most or all of the secondary amino hydrogen atoms available for subsequent reaction. These secondary amino hydrogen atoms are then reacted with glycidyl acrylate, glycidyl methacrylate, or a mixture thereof, in the presence of two different inhibitors. First, one must have present an inhibitor which retards the free-radical polymerization of ethylenic unsaturation, such as hydroquinone, the methyl ether of hydroquinone, beta-nitrostyrene and tertiary butyl catechol. Second, one must have present phenothiazine.

These two agents are both necessary to prevent excessive thickening and/or gelation. The difficulty here is a peculiar one. In extreme situations the reaction mixture will gel during the reaction. More frequently, gelation occurs after the reaction is completed and while the reaction product is being stored under conditions which would be thought to avoid any tendency to polymerize. The usual polymerization inhibitors are ineffective when used alone, so it is concluded that the polymerization which causes thickening and gelation is somehow related to the presence of amine groups in the product. When both of the specified agents are present, the viscosity increase is minimized and gelation is avoided. The mechanism for this result is not fully understood.

The preferred urea compound is 2-aminoethyl ethylene urea. Under preferred conditions, one molar proportion of this compound is reacted with one molar proportion of a saturated monoepoxide, preferably either propylene or butylene oxide. This first stage reaction consumes most of the primary amino hydrogen atoms which is essential to minimize Michael adduction. As a matter of interest, when glycidyl methacrylate was used in the Sandri et al. patent, the primary amino hydrogen atoms were unreacted when the glycidyl methacrylate was introduced. Under these conditions, the mixture of inhibitors used herein are not effective.

The first stage reaction product is then reacted with glycidyl acrylate or methacrylate (preferably the methacrylate is selected to further minimize Michael adduction) in the presence of the two inhibitors. These inhibitors should each be present in an amount of at least 0.02% based on the total weight of the reactants present. Preferred proportions are at least 0.05% of hydroquinone or the like, and at least 0.1% of the phenothiazine. One will use as little of these inhibitors as is effective, and the maximum proportion of use is simply to avoid such an excess of inhibitors as will prevent subsequent polymerization under normal polymerization conditions.

The avoidance of excessive viscosity increase can be judged by the fact that replacing glycidyl methacrylate with allyl glycidyl ether, the product viscosities are about the same. In contrast, using glycidyl methacrylate and eliminating the phenothiazine (while increasing the proportion of the other inhibitor to use the same total inhibitor concentration) the product is significantly more viscous, and the viscosity continues to increase on storage, gelling in a few weeks under even the most favorable conditions. In the absence of the hydroquinone, the phenothiazine alone is also ineffective, the viscosity of the product again increasing unduly with ultimate gelation being probable. How both inhibitors can function to accomplish what neither can do alone, regardless of any reasonable proportion of use, is not clear.

Referring more particularly to the saturated monoepoxides which may be used, propylene oxide is preferred and butylene oxide is very good, but other monoepoxides are fully useful, such as ethylene oxide, glycidyl esters of monocarboxylic acids, like Cardura E, butyl glycidyl ether and phenyl glycidyl ether. The saturated monoepoxide should be used in an amount of at least about 0.9 mole per mole of the aminoalkyl alkylene urea up to about 1.5 moles, preferably 1.0–1.3 moles.

The glycidyl acrylate or the preferred glycidyl methacrylate should be used in an amount of at least 0.8 up to about 2.0 molar proportions, preferably 0.9 to 1.4 molar proportions.

The temperature of reaction with the unsaturated monoepoxide is preferably held below 50° C. to further lower the viscosity increase. This extends the time of reaction. While most of the conditions in each reaction stage will be the same, the temperature is normally higher in the first stage since it has no gelation problem. All the amino hydrogen atoms are desirably consumed, and enough total monoepoxide is used for this purpose.

The aminoalkyl alkylene ureas which are used preferably have the amine group in the omega position and are known compounds. These are illustrated by 2-aminoethyl ethylene urea and 2-aminoethyl propylene urea. These compounds have the following structural formula:

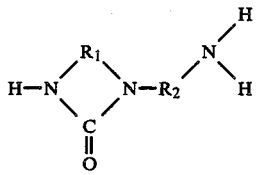

in which $R_1$ is alkylene having 2 or 3 carbon atoms, preferably 2 carbon atoms; and $R_2$ is alkylene having 2 to 10 carbon atoms, preferably 2 or 3 carbon atoms.

The aqueous emulsion copolymerization and the monoethylenically unsaturated monomers which are used in the copolymerization in accordance with the present invention are both matters of common and general knowledge. The emulsion copolymerization is illustrated in the examples herein, and suitable monomers are illustrated by acrylate esters, such as ethyl acrylate and butyl acrylate, methacrylate esters, like methyl methacrylate and butyl methacrylate, vinyl acetate, ethylene, acrylonitrile, and the like. These are usually balanced to give a glass transition temperature below about 20° C., usually between −10° C. and 10° C., as is well known in the art of latex paints. The pigmentation of these paints, usually with a pigment like titanium dioxide, rutile, is also conventional.

All proportions herein, including the examples and the claims, are by weight, unless otherwise stated.

EXAMPLE 195 grams of 2-aminoethyl ethylene urea are charged to a flask equipped with a reflux condenser and heated to 80° C. with agitation in the presence of 130 grams of toluene. Then, over a 2 hour period, 87.5 grams of 1,2-propylene oxide are added at 80° C. and this temperature is maintained for 1½ hours after the addition is complete. 1.51 equivalents of each reactant has been added and the reaction is essentially complete, so primary amino hydrogen atoms are largely consumed. The product is cooled to 40° C. and then 0.3 gram of hydroquinone and 0.6 gram of phenothiazine are added.

At this point, 214 grams (1.51 equivalents) of glycidyl methacrylate are added over a 2 hour period while maintaining 40° C. After the addition is complete, the reaction mixture is held at 40° C. to allow the reaction to proceed to substantial completion. 110 grams of butanol are than added at 40° C. over 15 minutes, and the solution product (solids content of 71%) is cooled to room temperature. This product is of low viscosity and is storage stable.

An aqueous emulsion copolymer was prepared using 84% of vinyl acetate, 14% n-butyl acrylate and 2% of the adhesion promoter of this example. The polymerization was carried out in conventional fashion using 4.4% of a nonionic surfactant constituted by 40 moles of ethylene oxide adducted with one mol of nonyl phenol, and 0.2% of an anionic surfactant constituted by sodium alkyl aryl polyether sulfonate (Triton X-200 made by Rohm & Haas may be used).

The polymerization was carried out at 53% solids to provide a latex having an average particle size of 0.2 micron. After pigmentation with titanium dioxide, rutile, and testing over a gloss alkyd surface, excellent adhesion was obtained. The emulsion was of excellent quality. Scrub resistance was also excellent.

Repeating the above example with glycidyl acrylate in place of glycidyl methacrylate produced satisfactory results, but some limited increase in viscosity of the adhesion-promoting monomer is observed.

The above examples are carried out with air present in the reactor while the unsaturated monoepoxide is being reacted. It is considered desirable, but not essential, to sparge air through the reactor contents while the unsaturated monoepoxide is reacted. The presence of oxygen helps to inhibit polymerization, but this is not considered to be essential.

What is claimed is:

1. An aqueous emulsion-copolymerized latex of copolymerized monoethylenically unsaturated monomers including from 0.1% to 10% of a copolymerizable monomer formed by reacting an omega aminoalkyl alkylene urea with about 0.9 up to about 1.3 molar proportions of a saturated monoepoxide to consume most or all of one of the two amino hydrogen atoms available on said alkylene urea, and then reacting with about 0.9 up to about 1.4 molar proportions of glycidyl acrylate, glycidyl methacrylate, or a mixture thereof in the presence of at least 0.02%, based on the total weight of the reactants present, of an inhibitor which retards the free-radical polymerization of ethylenic unsaturation, and phenothiazine.

2. A latex as recited in claim 1 in which one mol of 2-aminoethyl ethylene urea is reacted with about one molar proportion of propylene oxide or butylene oxide, and then the product of that reaction is reacted with about one molar proportion of glycidyl methacrylate in the presence of at least 0.05% of hydroquinone and at least 0.1% of phenothiazine.

3. A latex as recited in claim 2 in which said monoethylenically unsaturated monomers are selected to provide a glass transition temperature below about 20° C.

* * * * *